(12) United States Patent
Idkowiak-Baldys et al.

(10) Patent No.: US 10,034,826 B2
(45) Date of Patent: *Jul. 31, 2018

(54) PEPTIDES AND THEIR USE IN THE TREATMENT OF SKIN

(71) Applicant: Avon Products, Inc., Suffern, NY (US)

(72) Inventors: Jolanta Idkowiak-Baldys, Montebello, NY (US); Uma Santhanam, Tenafly, NJ (US)

(73) Assignee: Avon Products, Inc., Rye, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/844,095

(22) Filed: Sep. 3, 2015

(65) Prior Publication Data

US 2016/0175225 A1  Jun. 23, 2016

Related U.S. Application Data

(60) Provisional application No. 62/095,873, filed on Dec. 23, 2014.

(51) Int. Cl.

| A61Q 19/08 | (2006.01) |
|---|---|
| A61K 38/04 | (2006.01) |
| C07K 5/08 | (2006.01) |
| C07K 5/10 | (2006.01) |
| C07K 7/00 | (2006.01) |
| A61K 8/36 | (2006.01) |
| A61K 8/365 | (2006.01) |
| A61K 8/49 | (2006.01) |
| A61K 8/64 | (2006.01) |

(52) U.S. Cl.
CPC ............... *A61K 8/64* (2013.01); *A61Q 19/08* (2013.01); *A61K 8/36* (2013.01); *A61K 8/365* (2013.01); *A61K 8/49* (2013.01); *A61K 38/04* (2013.01); *C07K 5/08* (2013.01); *C07K 5/10* (2013.01)

(58) Field of Classification Search
None
See application file for complete search history.

(56) References Cited

U.S. PATENT DOCUMENTS

| 5,492,894 | A * | 2/1996 | Bascom | A61K 8/64 |
|---|---|---|---|---|
| | | | | 514/18.7 |
| 7,141,544 | B2 * | 11/2006 | Somers | A61K 38/05 |
| | | | | 424/85.1 |
| 7,674,451 | B2 * | 3/2010 | Dal Farra | A61K 8/64 |
| | | | | 424/401 |
| 9,125,843 | B2 * | 9/2015 | Pernodet | A61K 8/975 |
| 9,375,398 | B2 * | 6/2016 | Dreher | A61K 8/64 |
| 9,387,235 | B2 * | 7/2016 | Moussou | A61K 8/64 |
| 9,597,274 | B2 * | 3/2017 | Idkowiak-Baldys | A61K 8/64 |
| 2003/0134780 | A1 | 7/2003 | Patt | |
| 2004/0072341 | A1 * | 4/2004 | Katinger | C07C 237/22 |
| | | | | 435/325 |
| 2007/0134262 | A1 | 6/2007 | Mattner et al. | |
| 2009/0263402 | A1 | 10/2009 | Lee et al. | |
| 2012/0115938 | A1 | 5/2012 | Tabor et al. | |
| 2014/0105966 | A1 | 4/2014 | Bancel et al. | |
| 2015/0148297 | A1 | 5/2015 | Majeed et al. | |
| 2016/0367463 | A1 * | 12/2016 | Idkowiak-Baldys | A61K 8/64 |
| 2017/0281507 | A1 * | 10/2017 | Idkowiak-Baldys | A61K 8/64 |
| 2017/0281508 | A1 * | 10/2017 | Idkowiak-Baldys | A61K 8/64 |
| 2017/0304178 | A1 * | 10/2017 | Idkowiak-Baldys | A61K 8/64 |

FOREIGN PATENT DOCUMENTS

| WO | WO 2014/080376 | * | 5/2014 |
|---|---|---|---|
| WO | 2014/160496 A1 | | 10/2014 |
| WO | 2014161863 A1 | | 10/2014 |

OTHER PUBLICATIONS

Loffredo et al., Growth Differentiation Factor 11 is a Circulating Factor that Reverses Age-Related Cardiac Hypertrophy. Cell, 2013, 153, 828-839.
Sinha et al., Restoring Systemic GDF11 Levels Reverses Age-Related Dysfunction in Mouse Skeletal Muscle, Science, 2014, 344:649-52.
Villeda et al., Young blood reverses age-related impairments in cognitive function and synaptic plasticity in mice. Nat. Med. 2014;20:659-63.
Chauhan et al., Modeling signaling pathways leading to wrinkle formation: Identification of the skin aging target. Indian J. Dermatol Venereol Leprol, Sep.-Oct. 2009, vol. 75, Issue 5.
Mooney et al., PeptideLocator: Prediction of Bioactive Peptides in Protein Sequences, Bioinformatices, 2013, pp. 1-7.
U.S. Appl. No. 14/766,006, filed Aug. 5, 2015, J. Idkowiak-Baldys.
U.S. Appl. No. 14/767,451, filed Aug 12, 2015, J. Idkowiak-Baldys.
U.S. Appl. No. 14/767,805, filed Aug 13, 2015, J. Idkowiak-Baldys.
U.S. Appl. No. 14/742,060, filed Jun 17, 2015, J. Idkowiak-Baldys.

\* cited by examiner

*Primary Examiner* — Marianne P Allen
(74) *Attorney, Agent, or Firm* — Brian P. McCloskey; Elizabeth Morters

(57) ABSTRACT

Embodiments of the invention are related generally to the methods of diminishing the signs of aging in and/or improving health of human integuments, such as skin, and compositions comprising peptides useful therefor. The compositions according to the invention may comprise one or more peptides or fragments or derivatives thereof derived from a growth factor, e.g., Growth Differentiation Factor 11 (GDF11), in a topically acceptable vehicle.

13 Claims, No Drawings

SEQUENCE LISTING

```
<160> NUMBER OF SEQ ID NOS: 92

<210> SEQ ID NO 1
<211> LENGTH: 407
<212> TYPE: PRT
<213> ORGANISM: Homo sapiens

<400> SEQUENCE: 1

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160
```

```
Cys Cys His Phe His Phe Ser Pro Lys Val Met Thr Lys Val Leu
              165                 170                 175
Lys Ala Gln Leu Trp Val Tyr Leu Arg Pro Val Pro Arg Pro Ala Thr
        180                 185                 190
Val Tyr Leu Gln Ile Leu Arg Leu Lys Pro Leu Thr Gly Glu Gly Thr
            195                 200                 205
Ala Gly Gly Gly Gly Gly Arg Arg His Ile Arg Ile Arg Ser Leu
    210                 215                 220
Lys Ile Glu Leu His Ser Arg Ser Gly His Trp Gln Ser Ile Asp Phe
225                 230                 235                 240
Lys Gln Val Leu His Ser Trp Phe Arg Gln Pro Gln Ser Asn Trp Gly
                245                 250                 255
Ile Glu Ile Asn Ala Phe Asp Pro Ser Gly Thr Asp Leu Ala Val Thr
            260                 265                 270
Ser Leu Gly Pro Gly Ala Glu Gly Leu His Pro Phe Met Glu Leu Arg
        275                 280                 285
Val Leu Glu Asn Thr Lys Arg Ser Arg Arg Asn Leu Gly Leu Asp Cys
    290                 295                 300
Asp Glu His Ser Ser Glu Ser Arg Cys Cys Arg Tyr Pro Leu Thr Val
305                 310                 315                 320
Asp Phe Glu Ala Phe Gly Trp Asp Trp Ile Ile Ala Pro Lys Arg Tyr
                325                 330                 335
Lys Ala Asn Tyr Cys Ser Gly Gln Cys Glu Tyr Met Phe Met Gln Lys
            340                 345                 350
Tyr Pro His Thr His Leu Val Gln Gln Ala Asn Pro Arg Gly Ser Ala
        355                 360                 365
Gly Pro Cys Cys Thr Pro Thr Lys Met Ser Pro Ile Asn Met Leu Tyr
    370                 375                 380
Phe Asn Asp Lys Gln Gln Ile Ile Tyr Gly Lys Ile Pro Gly Met Val
385                 390                 395                 400
Val Asp Arg Cys Gly Cys Ser
                405

<210> SEQ ID NO 2
<211> LENGTH: 349
<212> TYPE: PRT
<213> ORGANISM: Homo sapiens

<400> SEQUENCE: 2

Met Thr Ala Ala Ser Met Gly Pro Val Arg Val Ala Phe Val Val Leu
1               5                   10                  15
Leu Ala Leu Cys Ser Arg Pro Ala Val Gly Gln Asn Cys Ser Gly Pro
                20                  25                  30
Cys Arg Cys Pro Asp Glu Pro Ala Pro Arg Cys Pro Ala Gly Val Ser
            35                  40                  45
Leu Val Leu Asp Gly Cys Gly Cys Cys Arg Val Cys Ala Lys Gln Leu
        50                  55                  60
Gly Glu Leu Cys Thr Glu Arg Asp Pro Cys Asp Pro His Lys Gly Leu
65                  70                  75                  80
Phe Cys Asp Phe Gly Ser Pro Ala Asn Arg Lys Ile Gly Val Cys Thr
                85                  90                  95
Ala Lys Asp Gly Ala Pro Cys Ile Phe Gly Gly Thr Val Tyr Arg Ser
            100                 105                 110
Gly Glu Ser Phe Gln Ser Ser Cys Lys Tyr Gln Cys Thr Cys Leu Asp
        115                 120                 125
```

```
Gly Ala Val Gly Cys Met Pro Leu Cys Ser Met Asp Val Arg Leu Pro
        130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 3
<211> LENGTH: 431
<212> TYPE: PRT
<213> ORGANISM: Homo sapiens

<400> SEQUENCE: 3

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
```

```
                145                 150                 155                 160
        Ser Lys Ile Pro Glu Gly Glu Ala Val Thr Ala Ala Glu Phe Arg Ile
                        165                 170                 175

Tyr Lys Asp Tyr Ile Arg Glu Arg Phe Asp Asn Glu Thr Phe Arg Ile
                        180                 185                 190

Ser Val Tyr Gln Val Leu Gln Glu His Leu Gly Arg Glu Ser Asp Leu
                        195                 200                 205

Phe Leu Leu Asp Ser Arg Thr Leu Trp Ala Ser Glu Glu Gly Trp Leu
                210                 215                 220

Val Phe Asp Ile Thr Ala Thr Ser Asn His Trp Val Asn Pro Arg
        225                 230                 235                 240

His Asn Leu Gly Leu Gln Leu Ser Val Glu Thr Leu Asp Gly Gln Ser
                        245                 250                 255

Ile Asn Pro Lys Leu Ala Gly Leu Ile Gly Arg His Gly Pro Gln Asn
                        260                 265                 270

Lys Gln Pro Phe Met Val Ala Phe Phe Lys Ala Thr Glu Val His Phe
                        275                 280                 285

Arg Ser Ile Arg Ser Thr Gly Ser Lys Gln Arg Ser Gln Asn Arg Ser
                290                 295                 300

Lys Thr Pro Lys Asn Gln Glu Ala Leu Arg Met Ala Asn Val Ala Glu
        305                 310                 315                 320

Asn Ser Ser Ser Asp Gln Arg Gln Ala Cys Lys Lys His Glu Leu Tyr
                        325                 330                 335

Val Ser Phe Arg Asp Leu Gly Trp Gln Asp Trp Ile Ile Ala Pro Glu
                        340                 345                 350

Gly Tyr Ala Ala Tyr Tyr Cys Glu Gly Glu Cys Ala Phe Pro Leu Asn
                        355                 360                 365

Ser Tyr Met Asn Ala Thr Asn His Ala Ile Val Gln Thr Leu Val His
                        370                 375                 380

Phe Ile Asn Pro Glu Thr Val Pro Lys Pro Cys Cys Ala Pro Thr Gln
        385                 390                 395                 400

Leu Asn Ala Ile Ser Val Leu Tyr Phe Asp Asp Ser Ser Asn Val Ile
                        405                 410                 415

Leu Lys Lys Tyr Arg Asn Met Val Val Arg Ala Cys Gly Cys His
                        420                 425                 430

<210> SEQ ID NO 4
<211> LENGTH: 241
<212> TYPE: PRT
<213> ORGANISM: Homo sapiens

<400> SEQUENCE: 4

Met Asn Arg Cys Trp Ala Leu Phe Leu Ser Leu Cys Cys Tyr Leu Arg
        1               5                   10                  15

Leu Val Ser Ala Glu Gly Asp Pro Ile Pro Glu Glu Leu Tyr Glu Met
                        20                  25                  30

Leu Ser Asp His Ser Ile Arg Ser Phe Asp Asp Leu Gln Arg Leu Leu
                        35                  40                  45

His Gly Asp Pro Gly Glu Glu Asp Gly Ala Glu Leu Asp Leu Asn Met
                        50                  55                  60

Thr Arg Ser His Ser Gly Gly Glu Leu Glu Ser Leu Ala Arg Gly Arg
        65                  70                  75                  80

Arg Ser Leu Gly Ser Leu Thr Ile Ala Glu Pro Ala Met Ile Ala Glu
                        85                  90                  95
```

```
Cys Lys Thr Arg Thr Glu Val Phe Glu Ile Ser Arg Arg Leu Ile Asp
                100                 105                 110
Arg Thr Asn Ala Asn Phe Leu Val Trp Pro Pro Cys Val Glu Val Gln
            115                 120                 125
Arg Cys Ser Gly Cys Cys Asn Asn Arg Asn Val Gln Cys Arg Pro Thr
        130                 135                 140
Gln Val Gln Leu Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
                165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
        195                 200                 205
Thr Ile Arg Thr Val Arg Val Arg Arg Pro Pro Lys Gly Lys His Arg
    210                 215                 220
Lys Phe Lys His Thr His Asp Lys Thr Ala Leu Lys Glu Thr Leu Gly
225                 230                 235                 240
Ala

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ile Leu Ser Lys Leu Arg Leu
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Arg Leu Lys
1

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Val Val
1

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Thr Ala Lys Asp Gly Ala Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Phe Gly Gly Thr Val Tyr Arg Ser
1               5

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Thr Pro Lys Ile Ser Lys Pro Ile Lys Phe Glu Leu Ser Gly
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Glu Cys Lys
1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ile Leu
1

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Leu Ser
1

<210> SEQ ID NO 14
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ser Lys
1

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Lys Leu
1

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Leu Arg
1

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Arg Leu
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Leu Ser
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Ser Lys
```

```
<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ser Lys Leu
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Lys Leu Arg
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Leu Arg Leu
1

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Arg Leu
1

<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Leu Lys
1

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 25

Thr Ala Lys
1

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Lys Asp
1

<210> SEQ ID NO 27
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Asp Gly
1

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Gly Ala
1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Pro
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Ala Lys Asp
1

<210> SEQ ID NO 31

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Lys Asp Gly
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Asp Gly Ala
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Gly Ala Pro
1

<210> SEQ ID NO 34
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Phe Gly
1

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gly
1

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

Gly Gly Thr
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Thr Val
1

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Val Tyr
1

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Tyr Arg
1

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Arg Ser
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Phe Gly Gly
1

<210> SEQ ID NO 42
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 42

Phe Gly Gly Thr
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Thr Val
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Thr Val Tyr
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Val Tyr Arg
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Tyr Arg Ser
1

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Thr Pro
1

```
<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Pro Lys
1

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Lys Ile
1

<210> SEQ ID NO 50
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Ile Ser
1

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Ser Lys
1

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Lys Pro
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

```
Lys Pro Ile
1

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Ile Lys
1

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Lys Phe
1

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Phe Glu
1

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Glu Leu
1

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Leu Ser
1

<210> SEQ ID NO 59
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 59

Leu Ser Gly
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Thr Pro Lys
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Pro Lys Ile
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Lys Ile Ser
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Ile Ser Lys
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Ser Lys Pro
1
```

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Lys Pro Ile
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Pro Ile Lys
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Ile Lys Phe
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Lys Phe Glu
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Phe Glu Leu
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Phe Glu Leu Ser
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Leu Ser Gly
1

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Phe Gly
1

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Gly Gly
1

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gly Thr
1

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Thr Val
1

<210> SEQ ID NO 76
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 76

Thr Val Tyr
1

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Tyr Arg
1

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Arg Ser
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Phe Gly Gly
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Gly Gly Thr
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Thr Val
1
```

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Thr Val Tyr
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Val Tyr Arg
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Tyr Arg Ser
1

<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Glu Cys
1

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Cys Lys
1

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 87

Gly Asp Ala Leu Gln Pro Glu
1               5

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Pro Glu Asp
1

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Ala Ser Ala Glu Pro Glu
1               5

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Lys Ile Glu
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asn Arg Asn Val
1

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Glu Asn Thr Lys Arg Ser
1               5
```

US 10,034,826 B2

PEPTIDES AND THEIR USE IN THE TREATMENT OF SKIN

CROSS-REFERENCE TO RELATED APPLICATIONS

This application claims priority to U.S. Provisional Patent Application Ser. No. 62/095,873, filed Dec. 23, 2014, the entirety of which is incorporated herein for all purposes.

SEQUENCE LISTING

The instant application contains a Sequence Listing which has been submitted electronically in ASCII format and is hereby incorporated by reference in its entirety. Said ASCII copy, created on Dec. 19, 2014, is named SC179P-US_S-L.txt and is 28,919 bytes in size.

FIELD OF INVENTION

The present invention relates generally to peptides comprising sequences homologous to fragments of certain human growth factors and their use in formulations and associated methods for improving the health and/or diminishing the dermatological signs of aging in human skin. In particular, the invention relates to peptides derived from human growth factors. These active peptides may promote the production of collagen and/or hyaluronic acid in human skin.

BACKGROUND

Growth factors are naturally occurring substances, usually proteins, that act as signaling molecules between cells. Their primary function is promoting cell differentiation and maturation. They play an important role in stimulating cell growth, proliferation, and wound healing. Many large classes, or superfamilies, of related growth factors are known.

Growth Differentiation Factor 11 (GDF11) is a protein belonging to the transforming growth factor (TGF) superfamily. Blood-derived GDF11 was recently shown to be involved in reverting aging phenotype in mice, including cardiac hypertrophy (see Loffredo et al., *Cell*, 2013, 153, 828-839), age-related sarcopenia (see Sinha et al., *Science*, 2014, 344:649-52), and decreased cognitive functions (see Villeda et al., *Nat. Med.* 2014; 20:659-63). Transforming growth factor beta (TGFβ) is another member of the TGF family. It controls proliferation, cellular differentiation, and other functions in most cells. Connective tissue growth factor (CTGF) is a protein of the CCN family of extracellular matrix-associated heparin-binding proteins. CTGF has important roles in many biological processes, including cell adhesion, migration, proliferation, angiogenesis, skeletal development, and tissue wound repair. It is thought that CTGF can cooperate with TGFβ, although the pathways remain largely unknown. Finally, platelet-derived growth factor (PDGF) is known to play a significant role in angiogenesis, the growth of blood vessels from already-existing blood vessel tissue.

Due to the many important roles growth factors play in maintaining healthy tissues, there has been some interest in using them in dermatological formulations. There are, however, drawbacks associated with the use of growth factors in topical formulations.

It is therefore an object of the invention to provide new peptides, derived from growth factors, and topical compositions containing them. It is also an object of the invention to provide methods for improving the health and/or appearance of skin, combatting signs of intrinsic and photoaging, and/or treating skin disorders. It is a further object of the invention to provide compositions and methods for treating, reversing, forestalling and/or ameliorating skin wrinkles and fine lines with cosmetic compositions comprising effective amounts of a peptide of the invention.

The foregoing discussion is presented solely to provide a better understanding of the nature of the problems confronting the art and should not be construed in any way as an admission as to prior art.

SUMMARY OF THE INVENTION

In accordance with the foregoing objectives and others, the present invention provides active peptides and topical formulations thereof that are useful for improving one or more signs of dermatological aging when topically applied to human integuments (skin, lips, nails, hair, etc.), particularly skin. The peptides of the invention are derived from human growth factors. In some embodiments, the peptides are capable of increasing collagen and/or HA production within skin cells and therefore will have a beneficial effect on reducing the appearance of aging on skin (e.g., diminishing the appearance of wrinkles and/or fine lines, tightening sagging skin, thickening thinning skin, evening skin tone, etc.).

Since using a full length growth factor (e.g., GDF11, or TGFβ, or CTGF, or PDFT) protein may present challenges, peptide sequences (e.g., 3-15 or 3-12 or 3-10 or 3-8 or 3-6 or 3-4 amino acids) derived from the sequence of full-length proteins have been designed. These peptides, especially peptides similar to putative functional regions of the protein, are contemplated to have antiaging benefits in skin.

One aspect of the invention provides compositions for topical use comprising one or more GDF11-derived peptides or fragments or derivatives thereof (e.g., having from about 3 to about 12 amino acids) of the invention in a physiologically acceptable carrier. Methods for ameliorating and/or preventing signs of human skin photo- and intrinsic aging comprising topically applying the compositions comprising one or more GDF11-derived peptides of the invention to the skin are also provided.

Another aspect of the invention provides compositions for topical use comprising one or more TGFβ-derived peptides or fragments or derivatives thereof (e.g., having from about 3 to about 12 amino acids) of the invention in a physiologically acceptable carrier. Methods for ameliorating and/or preventing signs of human skin photo- and intrinsic aging comprising topically applying the compositions comprising one or more TGFβ-derived peptides of the invention to the skin are also provided.

Yet another aspect of the invention provides compositions for topical use comprising one or more CTGF-derived peptides or fragments or derivatives thereof (e.g., having from about 3 to about 15 amino acids) of the invention in a physiologically acceptable carrier. Methods for ameliorating and/or preventing signs of human skin photo- and intrinsic aging comprising topically applying the compositions comprising one or more CTGF-derived peptides of the invention to the skin are also provided.

Yet another aspect of the invention provides compositions for topical use comprising one or more PDGF-derived peptides or fragments or derivatives thereof (e.g., having from about 3 to about 12 amino acids) of the invention in a physiologically acceptable carrier. Methods for ameliorating and/or preventing signs of human skin photo- and intrinsic aging comprising topically applying the compositions comprising one or more PDGF-derived peptides of the invention to the skin are also provided.

These and other aspects of the present invention will become apparent to those skilled in the art after a reading of

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

All percentages given herein refer to the weight percentages of a particular component relative to the entire composition, including the vehicle, unless otherwise indicated. It will be understood that the sum of all weight % of individual components within a composition will not exceed 100%.

All terms used herein are intended to have their ordinary meaning unless otherwise provided. The phrases "physiologically acceptable," "topically acceptable" and "dermatologically acceptable" are used interchangeably and are intended to mean that a particular component is generally regarding as safe and non-toxic for application to a human integument (e.g., skin) at the levels employed. The term "prevent," as used herein, includes delaying, slowing or forestalling the onset of or progression of a particular sign of skin aging. The phrase "individual in need thereof" refers to a human that could benefit from improved dermal appearance or health, including males or females. In some embodiments, the individual in need thereof is a female. The term "skin" includes, without limitation, the lips, skin of the face, hands, arms, neck, scalp, and chest. The term "thin" skin includes skin that is prematurely thinned, and may be diagnosed as such by a dermatologist. In some embodiments, the thin skin is skin of a female under the age of 40 or skin of a pre-menopausal female. As used herein, the term "consisting essentially of" is intended to limit the invention to the specified materials or steps and those that do not materially affect the basic and novel characteristics of the claimed invention, as understood from a reading of this specification.

As used herein, all terms are intended to have their ordinary meaning in the art unless specifically defined. The term "amino acid" is intended to include naturally occurring amino acids as well as non-naturally occurring amino acids and includes any small molecule (MW <1,000 Daltons) having at least one carboxyl group and at least one primary or secondary amine group capable of forming peptide bonds. The term "peptide" is intended to include any molecule comprising at least two amino acids joined by a peptide bond and therefore includes di-peptides, tri-peptides, oligopeptides, and polypeptides having up to about 20 amino acid residues. The term "peptide" also embraces structures having one or more linkers, spacers, or terminal groups which are not amino acids.

Peptides

The peptides of the invention comprise, consist essentially of, or consist of sequences derived from the Growth Differentiation Factor 11 (GDF11) protein or related proteins, such as TGFβ, CTGF, and/or PDGF, or of regions of homology of two or more proteins (e.g., regions of homology of GDF11 and TGFβ). Consisting essentially of, as used herein, is intended to mean that additional amino acids may be present at either terminus provided they do not substantially impair the activity of the peptide.

In one embodiment, the invention comprises any 3 or 4 consecutive amino acids derived from the sequence of Growth Differentiation Factor 11 (GDF11) precursor [*Homo sapiens*], NCBI Reference Sequence Accession No.: NP_005802.1, shown in Table 1 (SEQ ID NO: 1).

TABLE 1

| Sequence of GDF11 Precursor [*Homo Sapiens*] | | | | | |
|---|---|---|---|---|---|
| 1 | mvlaaplllg | flllalelrp | rgeaaegpaa | aaaaaaaaaa | agvggerssr papsvapepd |
| 61 | gcpvcvwrqh | srelrlesik | sqilsklrlk | eapnisrevv | kqllpkappl qqildlhdfq |
| 121 | gdalqpedfl | eedeyhatte | tvismaqetd | pavqtdgspl | cchfhfspkv mftkvlkaql |
| 181 | wvylrpvprp | atvylqilrl | kpltgegtag | ggggrrhir | irslkielhs rsghwqsidf |
| 241 | kqvlhswfrq | pqsnwgiein | afdpsgtdla | vtslgpgaeg | lhpfmelrvl entkrsrrnl |
| 301 | gldcdehsse | srccrypltv | dfeafgwdwi | iapkrykany | csgqceymfm qkyphthlvq |
| 361 | qanprgsagp | cctptkmspi | nmlyfndkqq | iiygkipgmv | vdrcgcs |

In some embodiments, the peptides of the invention comprise, consist essentially of, or consist of three or four consecutive amino acids from the sequence of GDF11 provided in Table 1. For example, the peptides of the invention may comprise three or four consecutive amino acids from the amino acids 1-10 or 11-20 or 21-30 or 31-40 or 41-50 or 51-60 or 61-70 or 71-80 or 81-90 or 91-100 or 101-110 or 111-120 or 121-130 or 131-140 or 141-150 or 151-160 or 161-170 or 171-180 or 181-190 or 191-200 or 201-210 or 211-220 or 221-230 or 231-240 or 241-250 or 251-260 or 261-270 or 271-280 or 281-290 or 291-300 or 301-310 or 311-320 or 321-330 or 331-340 or 341-350 or 351-360 or 361-370 or 371-380 or 381-390 or 391-400 or 401-407 of sequence of GDF11 provided in Table 1. In other embodiments, the peptides of the invention may comprise, consist essentially of, or consist of three or four consecutive amino acids from the amino acids 5-14 or 15-24 or 25-34 or 35-44 or 45-54 or 55-64 or 65-74 or 75-84 or 85-94 or 95-104 or 105-114 or 115-124 or 125-134 or 135-144 or 145-154 or 155-164 or 165-174 or 175-184 or 185-194 or 195-204 or 205-214 or 215-224 or 225-234 or 235-244 or 245-254 or 255-264 or 265-274 or 275-284 or 285-294 or 295-304 or 305-314 or 315-324 or 325-334 or 335-344 or 345-354 or 355-364 365-374 or 375-384 or 385-394 or 395-407 of sequence of GDF11 provided in Table 1.

In one embodiment, the invention comprises any 3 or 4 consecutive amino acids derived from the sequence of Connective Tissue Growth Factor (CTGF) [*Homo sapiens*], NCBI GenBank Accession No.: AAA91279.1, shown in Table 2 (SEQ ID NO: 2).

TABLE 2

| Sequence of CTGF [Homo Sapiens] | | | | | |
|---|---|---|---|---|---|
| 1 | mtaasmgpvr | vafvvllalc | srpavgqncs | gpcrcpdepa | prcpagvslv ldgcgccrvc |
| 61 | akqlgelcte | rdpcdphkgl | fcdfgspanr | kigvctakdg | apcifggtvy rsgesfqssc |
| 121 | kyqctcldga | vgcmplcsmd | vrlpspdcpf | prrvklpgkc | ceewvcdepk dqtvvgpala |
| 181 | ayrledtfgp | dptmirancl | vqttewsacs | ktcgmgistr | vtndnascrl ekqsrlcmvr |
| 241 | pceadleeni | kkgkkcirtp | kiskpikfel | sgctsmktyr | akfcgvctdg rcctphrttt |
| 301 | lpvefkcpdg | evmkknmmfi | ktcachyncp | gdndifesly | yrkmygdma |

In some embodiments, the peptides of the invention comprise, consist essentially of, or consist of three or four consecutive amino acids from the sequence of CTGF provided in Table 2. For example, the peptides of the invention may comprise three or four consecutive amino acids from the amino acids 1-10 or 11-20 or 21-30 or 31-40 or 41-50 or 51-60 or 61-70 or 71-80 or 81-90 or 91-100 or 101-110 or 111-120 or 121-130 or 131-140 or 141-150 or 151-160 or 161-170 or 171-180 or 181-190 or 191-200 or 201-210 or 211-220 or 221-230 or 231-240 or 241-250 or 251-260 or 261-270 or 271-280 or 281-290 or 291-300 or 301-310 or 311-320 or 321-330 or 331-340 or 341-349 of sequence of CTGF provided in Table 2. In other embodiments, the peptides of the invention may comprise, consist essentially of, or consist of three or four consecutive amino acids from the amino acids 5-14 or 15-24 or 25-34 or 35-44 or 45-54 or 55-64 or 65-74 or 75-84 or 85-94 or 95-104 or 105-114 or 115-124 or 125-134 or 135-144 or 145-154 or 155-164 or 165-174 or 175-184 or 185-194 or 195-204 or 205-214 or 215-224 or 225-234 or 235-244 or 245-254 or 255-264 or 265-274 or 275-284 or 285-294 or 295-304 or 305-314 or 315-324 or 325-334 or 335-344 or 345-349 of sequence of CTGF provided in Table 2.

In one embodiment, the invention comprises any 3 or 4 consecutive amino acids derived from the sequence of Transforming Growth Factor-beta (TGFβ) [*Homo sapiens*] NCBI GenBank Accession No.: AAA36738.1, shown in Table 3 (SEQ ID NO: 3).

In some embodiments, the peptides of the invention comprise, consist essentially of, or consist of three or four consecutive amino acids from the sequence of TGFβ provided in Table 3. For example, the peptides of the invention may comprise three or four consecutive amino acids from the amino acids 1-10 or 11-20 or 21-30 or 31-40 or 41-50 or 51-60 or 61-70 or 71-80 or 81-90 or 91-100 or 101-110 or 111-120 or 121-130 or 131-140 or 141-150 or 151-160 or 161-170 or 171-180 or 181-190 or 191-200 or 201-210 or 211-220 or 221-230 or 231-240 or 241-250 or 251-260 or 261-270 or 271-280 or 281-290 or 291-300 or 301-310 or 311-320 or 321-330 or 331-340 or 341-350 or 351-360 or 361-370 or 371-380 or 381-390 or 391-400 or 401-410 or 411-420 or 421-431 of sequence of TGFβ provided in Table 3. In other embodiments, the peptides of the invention may comprise, consist essentially of, or consist of three or four consecutive amino acids from the amino acids 5-14 or 15-24 or 25-34 or 35-44 or 45-54 or 55-64 or 65-74 or 75-84 or 85-94 or 95-104 or 105-114 or 115-124 or 125-134 or 135-144 or 145-154 or 155-164 or 165-174 or 175-184 or 185-194 or 195-204 or 205-214 or 215-224 or 225-234 or 235-244 or 245-254 or 255-264 or 265-274 or 275-284 or 285-294 or 295-304 or 305-314 or 315-324 or 325-334 or 335-344 or 345-354 or 355-364 or 365-374 or 375-384 or 385-394 or 395-404 or 405-414 or 415-424 or 425-431 of sequence of TGFβ provided in Table 3.

In one embodiment, the invention comprises any 3 or 4 consecutive amino acids derived from the sequence of Platelet-Derived Growth Factor (PDGF) [*Homo sapiens*] (NCBI GenBank Accession No.: AAA60552.1), shown in Table 4 (SEQ ID NO: 4).

TABLE 3

| Sequence of TGFβ [Homo Sapiens] | | | | | |
|---|---|---|---|---|---|
| 1 | mhvrslraaa | phsfvalwap | lfllrsalad | fsldnevhss | fihrrlrsqe rremqreils |
| 61 | ilglphrprp | hlqgkhnsap | mfmldlynam | aveegggpgg | qgfsypykav fstqgpplas |
| 121 | lqdshfltda | dmvmsfvnlv | ehdkeffhpr | yhhrefrfdl | skipegeavt aaefriykdy |
| 181 | irerfdnetf | risvyqvlqe | hlgresdlfl | ldsrtlwase | egwlvfdita tsnhwvvnpr |
| 241 | hnlglqlsve | tldgqsinpk | lagligrhgp | qnkqpfmvaf | fkatevhfrs irstgskqrs |
| 301 | qnrsktpknq | ealrmanvae | nsssdqrqac | kkhelyvsfr | dlgwqdwiia pegyaayyce |
| 361 | gecafplnsy | mnatnhaivq | tlvhfinpet | vpkpccaptq | lnaisvlyfd dssnvilkky |
| 421 | rnmvvracgc | h | | | |

TABLE 4

Sequence of PDGF [Homo Sapiens]

```
  1  mnrcwalfls  lccylrlvsa  egdpipeely  emlsdhsirs  fddlqrllhg  dpgeedgael 61  dlnmtrshsg  geleslargr  rslgsltiae  pamiaecktr  tevfeisrrl  idrtnanflv 121  wppcvevqrc  sgccnnrnvq  crptqvqlrp  vqvrkieivr  kkpifkkatv  tledhlackc 181  etvaaarpvt  rspggsgeqr  aktpqtrvti  rtvrvrrppk  gkhrkfkhth  dktalketlg 241  a
```

In some embodiments, the peptides of the invention comprise, consist essentially of, or consist of three or four consecutive amino acids from the sequence of PDGF provided in Table 4. For example, the peptides of the invention may comprise three or four consecutive amino acids from the amino acids 1-10 or 11-20 or 21-30 or 31-40 or 41-50 or 51-60 or 61-70 or 71-80 or 81-90 or 91-100 or 101-110 or 111-120 or 121-130 or 131-140 or 141-150 or 151-160 or 161-170 or 171-180 or 181-190 or 191-200 or 201-210 or 211-220 or 221-230 or 231-241 of sequence of PDGF provided in Table 4. In other embodiments, the peptides of the invention may comprise, consist essentially of, or consist of three or four consecutive amino acids from the amino acids 5-14 or 15-24 or 25-34 or 35-44 or 45-54 or 55-64 or 65-74 or 75-84 or 85-94 or 95-104 or 105-114 or 115-124 or 125-134 or 135-144 or 145-154 or 155-164 or 165-174 or 175-184 or 185-194 or 195-204 or 205-214 or 215-224 or 225-234 or 235-241 of sequence of PDGF provided in Table 4.

In some embodiments, the peptides of the invention are derived from regions of homology between any two of GDF11, TGFb, CTGF, and PDGF. In some embodiments, the regions of homology may span from 3-16 or 3-12 or 3-8 or 3-6 consecutive amino acids in the sequences. In some embodiments, the regions of homology may span from 4-16 or 4-12 or 4-8 or 4-6 consecutive amino acids in the sequences. These regions may be at least 50%, or at least 60%, or at least 70%, or at least 80%, or at least 90% homologous.

In some embodiments the peptides according to the invention exclude the peptides having Sequence ID NOs 5-86. In another embodiment exclude peptide having Sequence ID NOs 87-92.

One aspect of the invention provides peptides derived from GDF11 having the following sequence: QILSKLRL (Gln-Ile-Leu-Ser-Lys-Leu-Arg-Leu) (SEQ ID NO: 5), LRLK (Leu-Arg-Leu-Lys) (SEQ ID NO: 6), and MVV (Met-Val-Val) (SEQ ID NO: 7).

Another aspect of the invention provides peptides derived from TGFβ having the following sequence: QILSKLRL (Gln-Ile-Leu-Ser-Lys-Leu-Arg-Leu) (SEQ ID NO: 5), LRLK (Leu-Arg-Leu-Lys) (SEQ ID NO: 6).

Another aspect of the invention provides peptides derived from CTGF having the following sequence: TAKDGAP (Thr-Ala-Lys-Asp-Gly-Ala-Pro) (SEQ ID NO: 8), IFGGT-VYRS (Ile-Phe-Gly-Gly-Thr-Val-Tyr-Arg-Ser) (SEQ ID NO: 9), and RTPKISKPIKFELSG (Arg-Thr-Pro-Lys-Ile-Ser-Lys-Pro-Ile-Lys-Phe-Glu-Leu-Ser-Gly) (SEQ ID NO: 10).

Yet another aspect of the invention provides peptides derived from PDGF having the following sequence: AECK (Ala-Glu-Cys-Lys) (SEQ ID NO: 11).

Peptides of the invention may have one or more additional amino acids joined to the amino and/or carboxy terminus via peptide bonds. In some embodiments, the peptides will comprise a hydrocarbon chain on the amino and/or carboxyl terminus, including, without limitation, $C_{1-24}$ or $C_{6-18}$ or $C_{12-18}$ aliphatic hydrocarbons, which may be straight chained or branched or cyclic. In some embodiments, the peptides include the reaction product of a peptide with a fatty acid or fatty alcohol. For example, the N-terminus may be reacted with a $C_{6-24}$ fatty acid (e.g., palmitic acid) to form an amide bond. The carboxyl terminus may be reacted with a $C_{6-24}$ fatty alcohol (e.g., cetyl alcohol) to form an ester. These fatty derivatives may improve the lipophilicity of the peptide. The phrase "consisting essentially of," as used herein, is intended to mean that additional amino acids or other residues may be present at either terminus of the peptide and/or on a side chain provided they do not substantially impair the activity of the peptide to stimulate collagen and/or HA production.

Topically acceptable salts, esters, and prodrugs (collectively "derivatives") of the peptides of the invention are also suitable. The esters may include $C_{1-24}$ aliphatic hydrocarbon esters of the carboxyl terminus and/or the carboxyl side chain, including $C_{1-24}$ or $C_{1-18}$ or $C_{1-16}$ or $C_{1-12}$ or $C_{1-6}$ alkyl esters. Salts will typically be acid addition salts formed by the reaction of the peptide with an inorganic or an organic acid. Inorganic acids include mineral acids such as HCl and $H_2SO_4$, and the like. Organic acids include citric, benzoic, tartaric, malic, maleic, succinic, acetic, and propionic acid. Prodrugs include any esters or amides that hydrolyze in vivo to yield the peptide of formula (I). Examples of suitable prodrugs can be found in the book entitled "Prodrugs and Targeted Delivery: Towards Better ADME Properties," Volume 47 (2011), published by WILEY-VCH Verlag & Co, which is herein incorporated by reference in its entirety. In one embodiment, the prodrug is formed by reacting the peptide with glyoxylic acid to produce peptidyl-α-hydroxylglycine derivatives having improved stability. In other embodiment the prodrugs may include terminal N-acetyl derivatives, side chain N-acetyl derivatives, N-hydroxy methylation or N-phthalidation of its N-terminus and/or side chain. In some embodiments either terminus may be functionalized with an amino acid of the form $H_2N—(CH_2)_n—CO_2H$ where "n" is an integer from 1-10, including amino valeric acid. In some embodiments, a lysine-amino valeric acid group is added at either terminus through a peptide bond.

Fragments of the peptides of the invention are also contemplated. Fragments, as used herein, are defined as having at least 3 aminoacids of the peptide sequence from which they are derived.

In one aspect, the following tripeptide fragments of the peptide derived from GDF11 and having the sequence QILSKLRL (SEQ ID NO: 5) are contemplated: QIL (Gln-Ile-Leu) (SEQ ID NO: 12), ILS (Ile-Leu-Ser) (SEQ ID NO: 13), LSK (Leu-Ser-Lys) (SEQ ID NO: 14), SKL (Ser-Lys- Leu) (SEQ ID NO: 15), KLR (Lys-Leu-Arg) (SEQ ID NO: 16), and LRL (Leu-Arg-Leu) (SEQ ID NO: 17). Tetrapeptide fragments include the following sequences: QILS (Gln-Ile-Leu-Ser) (SEQ ID NO: 18), ILSK (Ile-Leu-Ser-Lys) (SEQ ID NO: 19), LSKL (Leu-Ser-Lys-Leu) (SEQ ID NO: 20), SKLR (Ser-Lys-Leu-Arg) (SEQ ID NO: 21), and KLRL (Lys-Leu-Arg-Leu) (SEQ ID NO: 22) or derivatives of such peptides.

In another aspect, the following tripeptide fragments of the peptide derived from GDF11 and having the sequence LRLK (SEQ ID NO: 6) are contemplated: LRL (Leu-Arg-Leu) (SEQ ID NO: 23) and RLK (Arg-Leu-Lys) (SEQ ID NO: 24), and derivatives of such peptides.

In yet another aspect, the following tripeptide fragments of the peptide derived from CTGF and having the sequence TAKDGAP (SEQ ID NO: 8) are contemplated: TAK (Thr-Ala-Lys) (SEQ ID NO: 25), AKD (Ala-Lys-Asp) (SEQ ID NO: 26), KDG (Lys-Asp-Gly) (SEQ ID NO: 27), DGA (Asp-Gly-Ala) (SEQ ID NO: 28), and GAP (Gly-Ala-Pro) (SEQ ID NO: 29) or derivatives thereof. Tetrapeptide fragments include the following sequences: TAKD (Thr-Ala-Lys-Asp) (SEQ ID NO: 30), AKDG (Ala-Lys-Asp-Gly) (SEQ ID NO: 31), KDGA (Lys-Asp-Gly-Ala) (SEQ ID NO: 32), and DGAP (Asp-Gly-Ala-Pro) (SEQ ID NO: 33) or derivatives thereof.

In yet another aspect, the following tripeptide fragments of the peptide derived from CTGF and having the sequence IFGGTVYRS (SEQ ID NO: 9) are contemplated: IFG (SEQ ID NO: 34), FGG (SEQ ID NO: 35), GGT (SEQ ID NO: 36), GTV (SEQ ID NO: 37), TVY (SEQ ID NO: 38), VYR (SEQ ID NO: 39), and YRS (SEQ ID NO: 40) or derivatives thereof. Tetrapeptide fragments include the following sequences: IFGG (SEQ ID NO: 41), FGGT (SEQ ID NO: 42), GGTV (SEQ ID NO: 43), GTVY (SEQ ID NO: 44), TVYR (SEQ ID NO: 45), and VYRS (SEQ ID NO: 46) or derivatives thereof.

In yet another aspect, the following tripeptide fragments of the peptide derived from CTGF and having the sequence RTPKISKPIKFELSG (SEQ ID NO: 10) are contemplated: RTP (SEQ ID NO: 47), TPK (SEQ ID NO: 48), PKI (SEQ ID NO: 49), KIS (SEQ ID NO: 50), ISK (SEQ ID NO: 51), SKP (SEQ ID NO: 52), KPI (SEQ ID NO: 53), PIK (SEQ ID NO: 54), IKF (SEQ ID NO: 55), KFE (SEQ ID NO: 56), FEL (SEQ ID NO: 57), ELS (SEQ ID NO: 58), and LSG (SEQ ID NO: 59) or derivatives thereof. Tetrapeptide fragments include the following sequences: RTPK (SEQ ID NO: 60), TPKI (SEQ ID NO: 61), PKIS (SEQ ID NO: 62), KISK (SEQ ID NO: 63), ISKP (SEQ ID NO: 64), SKPI (SEQ ID NO: 65), KPIK (SEQ ID NO: 66), PIKF (SEQ ID NO: 67), IKFE (SEQ ID NO: 68), KFEL (SEQ ID NO: 69), FELS (SEQ ID NO: 70), and ELSG (SEQ ID NO: 71) or derivatives thereof.

In yet another aspect, the following tripeptide fragments of the peptide derived from CTGF and having the sequence IFGGTVYRS (SEQ ID NO: 9) are contemplated: IFG (SEQ ID NO: 72), FGG (SEQ ID NO: 73), GGT (SEQ ID NO: 74), GTV (SEQ ID NO: 75), TVY (SEQ ID NO: 76), VYR (SEQ ID NO: 77), and YRS (SEQ ID NO: 78) or derivatives thereof. Tetrapeptide fragments include the following sequences: IFGG (SEQ ID NO: 79), FGGT (SEQ ID NO: 80), GGTV (SEQ ID NO: 81), GTVY (SEQ ID NO: 82), TVYR (SEQ ID NO: 83), and VYRS (SEQ ID NO: 84) or derivatives thereof.

In another aspect, the following tripeptide fragments of the peptide derived from PDGF and having the sequence AECK (SEQ ID NO: 11) are contemplated: AEC (SEQ ID NO: 85) and ECK (SEQ ID NO: 86) or derivatives thereof.

A peptide comprising peptides of the invention (e.g., SEQ ID NOs: 5-86) or fragments or derivatives thereof, may have one or more additional amino acids joined to the amino and/or carboxy terminus via peptide bonds. In some embodiments, the peptides or fragments thereof (SEQ ID NOs: 5-86) will have from 3 to 20 or from 3 to 16 or from 3 to 12 or from 3 to 10 or from 3-9 or from 3-8 or from 3-7 or from 3-6 amino acids. In some embodiments, the peptides will comprise a hydrocarbon chain on the amino and/or carboxyl terminus, including, without limitation, $C_{1-24}$ or $C_{6-18}$ or $C_{12-18}$ aliphatic hydrocarbons, which may be straight chained or branched or cyclic. In some embodiments, the peptides include the reaction product of a peptide with a fatty acid or fatty alcohol. For example, the N-terminus may be reacted with a $C_{6-24}$ fatty acid (e.g., palmitic acid) to form an amide bond. The carboxyl terminus may be reacted with a $C_{6-24}$ fatty alcohol (e.g., cetyl alcohol) to form an ester. These fatty derivatives may improve the lipophilicity of the peptide. The phrase "consisting essentially of," as used herein, is intended to mean that additional amino acids or other residues may be present at either terminus of the peptide and/or on a side chain provided they do not substantially impair the activity of the peptide to stimulate collagen production.

It is well within the skill in the art to prepare peptides using, for example, conventional protection and activation chemistry. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), tert-butoxycarbonyl (t-Boc), and 9-flourenylmethloxycarbonyl (FMOC). The carboxyl group may be protected by forming an acid or base labile ester such as a methyl, ethyl, benzyl, or trimethylsilyl esters. After protection, the first and second amino acids are reacted in a suitable solvent such as water or DMF in the presence of an in situ activating agent such as N,N'-dicyclohexylcarbodiimide (DCCI), diisopropylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as tert-butyl or benzyl for OH and SH; methyl, ethyl, tert-butyl or benzyl for carboxyl groups, and 2,2,5,7,8-pentamethylchroman-6-sulphonyl for the —NHC(NH$_2$)=NH functionality of Arg. Following the coupling reaction, selective deprotection of the amino group of the first amino acid is accomplished by acid hydrolysis under conditions that do not remove the carboxyl protecting group of the second amino acid. The procedure is repeated with additional amino protected amino acids. Solid phase synthesis, such as the well-known Merrifield method, is especially useful for synthesizing the peptides of the invention. Lysine-amino valeric acid (K-ava) derivatives are described in U.S. Pat. No. 8,551,956, the disclosure of which is hereby incorporated by reference.

Topical Compositions

The compositions according to the invention may be formulated in a variety of forms for topical application and will typically comprise from about 0.000001% by weight to about 20% by weight of the peptide. More typically, the peptide will comprise from about 0.00001% by weight to about 10% by weight, and more preferably from about 0.00001% by weight to about 5% by weight of the composition. In one embodiment, the active peptide or a fragment or derivative thereof will comprise from about 0.00001% by weight to about 0.0001% by weight or to about 0.001% by weight or to about 0.1% by weight of the composition. The compositions may comprise an effective amount of the peptide, by which is meant an amount sufficient to stimulate production of collagen in the skin. In other embodiments, the amount of peptide or a fragment or derivative thereof will be sufficient to diminish the appearance of dermatological signs of aging in a given area of skin when topically applied thereto daily for a period of at least eight weeks.

The peptides of the invention (e.g., SEQ ID NOs: 5-86) are provided in physiologically acceptable vehicles or carriers. The vehicle may be either hydrophobic or hydrophilic. Suitable, hydrophobic carriers include, for example, waxy non-ionic substances commonly used in cosmetics, such as esters and ethers of fatty alcohols and of fatty acids, with carbon chain length from $C_4$ to $C_{22}$, preferably from $C_8$ to $C_{18}$, or from $C_{12}$ to $C_{18}$.

Examples of a fatty hydrophobic carriers include isopropyl myristate, isopropyl palmitate, octyl palmitate, isopropyl lanolate, acetylated lanolin alcohol, the benzoate of $C_{12}$-$C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, isopropyl isostearate, and the like.

Suitable hydrophilic carriers may comprise, for example, water, lower alcohols ($C_{1-6}$), glycols and alkoxylated glycols commonly used in cosmetics, including ethylene glycol, diethylene glycol, triethylene glycol, propylene glycol, dipropylene glycol, and the like.

The topically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, or a gellant, typically in an amount from about 0.001% to about 5% by weight.

The topically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 50% to about 99% by weight of the composition.

In one embodiment of the invention, the compositions may include one or more additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few. The amounts of these various ingredients are those conventionally used in the cosmetic field to achieve their intended purpose, and range individually or collectively typically from about 0.001 wt % to about 20 wt % by weight of the composition. The nature of these ingredients and their amounts must be compatible with the production and function of the compositions of the disclosure.

Exemplary anti-aging components include, without limitation, botanicals (e.g., *Butea frondosa* extract, *Tiliacora triandra* extract, *Portulaca oleracea, Melicope elleryana*, etc.); phytol; phytonic acid; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA) in amounts effective to stabilize the retinoid (e.g., 0.0001%-5%).

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, and vegetable gums such as xanthan gum; gelling agents, such as ester-terminated polyester amides; structuring agents; metal chelating agents such as EDTA or salts thereof; pigments; colorants; and pH adjusters (citric acid, ethanolamine, sodium hydroxide, etc.). The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. The foregoing may individually or collectively comprise from about 0.0001% to about 20% by weight of the composition.

In addition, the compositions contemplated by this disclosure can include one or more compatible cosmetically acceptable adjuvants commonly used and known by the skilled practitioner, such as colorants, pearls, chromalites, micas, pigments, dyes, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals. The topical compositions of the present disclosure may also include a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

A sunscreen may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

In one embodiment, the topical composition will have a pH range from 1 to 13, with a pH in the range of from 2 to 12 being typical. In some embodiment, the composition will have a pH in the range of from 3.5 to 7 or from 7-10.5. In some embodiments, the pH will be in the range of 3-4, or 4-5, or 5-6, or 6-7, or 7-8, or 8-9, or 9-10, or 10-11, or 11-12. Suitable pH adjusters such as sodium hydroxide, citric acid and triethanolamine may be added to bring the pH within the desired range.

Another embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

The compositions may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The invention also provides a method for ameliorating and/or preventing signs of human skin photo- and intrinsic aging comprising topically applying the compositions of the invention. The compositions of the invention are preferably applied to affected skin areas once or twice daily for as long as is necessary to achieve desired anti-aging results.

Methods of Treatment

Methods are provided for enhancing the production of collagen and/or HA in human skin comprising topically applying to an area of the skin in need thereof (e.g., sagging skin, thinning skin, skin suffering from wrinkles and fine lines, etc.) a topical composition comprising a topically acceptable vehicle, and an effective amount of a peptide of the invention (e.g., SEQ ID NOs: 5-86), for a time sufficient to improve the appearance thereof. The treatment may be at least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid or a derivative) in amounts effective to improve the appearance of skin.

In another aspect of the invention, the compositions are applied topically to improve the aesthetic appearance of human skin. The method comprises topically applying to an area of the skin in need thereof a composition comprising an effective amount of a peptide of the invention (e.g., SEQ ID NOs: 5-86) for a time sufficient to improve the aesthetic appearance of said human skin. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more.

The aesthetic improvement of human skin may be an improvement of any attribute or characteristic of skin, including without limitation:

(a) treatment, reduction, and/or prevention of fine lines or wrinkles;

(b) reduction of skin pore size;

(c) improvement in skin thickness, plumpness, and/or tautness;

(d) improvement in skin smoothness, suppleness and/or softness;

(e) improvement in skin tone, radiance, and/or clarity;

(f) improvement in procollagen, and/or collagen production;

(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition comprising a peptide of the invention (e.g., SEQ ID NOs: 5-86), for a time sufficient to improve the aesthetic appearance of said human skin. The treatment may be a least once or twice daily and may last for a period of at least four weeks, typically at least eight weeks or longer. The composition may optionally further comprise a retinoid (e.g., retinol or retinyl palmitate) and/or an alpha-hydroxy acid (e.g., glycolic acid) and/or a beta-hydroxy acid (e.g., salicylic acid or derivative) in amounts effective to improve the appearance of skin.

In yet another aspect of the invention, methods are provided for reducing the severity of, reducing the number of, or preventing or forestalling the onset of, wrinkles or fine lines on human skin comprising topically applying to an area of the skin in need thereof (e.g., wrinkled skin), an effective amount (e.g., 0.001%-1% by weight, w/w) of a peptide of the invention (e.g., SEQ ID NOs: 5-86) in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid).

The invention provides a method for treating aging skin by topically applying a composition comprising a collagen-stimulating peptide (e.g., SEQ ID NOs: 5-86), typically in a physiologically acceptable vehicle, over the affected area for a period of time sufficient to remediate, reverse, reduce, ameliorate, or prevent dermatological signs of aging. Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

In some embodiments, the peptides of the invention (e.g., SEQ ID NOs: 5-86) will be used to reduce the severity of fine lines or wrinkles, often in combination with retinol. The composition will typically be applied to the skin one, two, or three times daily for as long as is necessary to achieve desired results. The treatment regimen may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

It is also contemplated that the compositions of the invention will be useful for treating thin skin by topically applying the composition comprising the active peptides (e.g., SEQ ID NOs: 5-86) to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention comprising active peptides (e.g., SEQ ID NOs: 5-86) are applied to human skin to reduce sebum production or improve the appearance of skin affected by cellulite, and/or reduce unwanted lipogenesis or increase lipolysis. In this embodiment, the peptides of the invention can be formulated in topically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, *perilla* oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

In certain embodiments, the compositions described herein comprising active peptides (e.g., SEQ ID NOs: 5-86) can be used to treat and/or prevent hyper-pigmentation of skin and/or of the hair, for example, to lighten skin or hair. In some embodiments, the compositions are topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, for example, skin tanned due to UV exposure. Hyper-pigmented hair includes any shade of hair that is darker than desired.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In another embodiment, the peptides of the invention (e.g., SEQ ID NOs: 5-86) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms (including lyophilized powders of the peptide suitable for reconstitution with water). Pharmaceutical dosage forms will typically include from about 0.1 mg to about 200 mg, or from about 1 mg to about 100 mg of the peptides of the invention. The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

EXAMPLES

The following example illustrates a specific aspect of the instant description. The example should not be construed as limiting, as the example merely provides specific understanding and practice of the embodiments and its various aspects.

Example 1

The peptides of the invention were synthesized by GenScript (Piscataway, N.J.).

Human dermal fibroblast cells were grown in a 96 well plate in DMEM media (available from Corning, N.Y.) supplemented with 10% Fetal Bovine Serum (FBS) and L-glutamine (0.07×105 cells/plate). After reaching about 75% confluence, cells were transferred into DMEM media without FBS and incubated for 4-6 hours. Next, cells were treated with a peptide at 0.00001%, 0.0001%, 0.001% final concentration in DMEM media without FBS for 48 h. After treatment the media were collected, and cell viability was measured using MTT. Amount of collagen secreted was tested in the media using HTRF human pro-collagen I kit (available from Cisbio Inc., Bedford, Mass.). Amount of secreted Hyaluronic Acid (HA) was tested in the media using HA Elisa kit (available from Corgenix, Broomfield, Colo.).

Results are summarized in Table 5 below as percent change of pro-collagen I and/or HA production relative to vehicle control using the following keys with the peptide concentration provided in parentheses:
Pro-Collagen I Increase Key: 0: <10%, +: 10-30%, ++: 30-50%, +++: 50-70%, ++++: >70%
HA Increase Key: 0: <20%, +: 20-50%, ++: 50-90%, +++: 90-150%, ++++: >150%

TABLE 5

| Peptide Sequence | Origin | Increase in Pro-Collagen I Production | Increase in HA Production |
|---|---|---|---|
| GDALQPE (SEQ ID NO: 87) | GDF11 | 0 | 0 |
| QPED (SEQ ID NO: 88) | GDF11 | 0 | 0 |
| QILSKLRL (SEQ ID NO: 5) | GDF11 and TGFβ | +(0.001%) | 0 |

TABLE 5-continued

| Peptide Sequence | Origin | Increase in Pro-Collagen I Production | Increase in HA Production |
|---|---|---|---|
| LRLK (SEQ ID NO: 6) | GDF11 and TGFβ | 0 | +(0.001%) |
| MVV (SEQ ID NO: 7) | GDF11 and TGFβ | 0 | +(0.0001%) |
| EASAEPE (SEQ ID NO: 89) | TGFβ | 0 | 0 |
| TAKDGAP (SEQ ID NO: 8) | CTGF | +(0.00001%) | ++(0.001%) |
| IFGGTVYRS (SEQ ID NO: 9) | CTGF | +(0.001%) | ++(0.001%) |
| RTPKISKPIKFELSG (SEQ ID NO: 10) | CTGF | 0 | +(0.001%) |
| RKIE (SEQ ID NO: 90) | PDGF | 0 | 0 |
| AECK (SEQ ID NO: 11) | PDGF | 0 | +++(0.001%) |
| NRNV (SEQ ID NO: 91) | PDGF | 0 | 0 |
| LENTKRS (SEQ ID NO: 92) | GDF11 and TGFβ | 0 | 0 |

As shown in Table 5, peptides of the invention effectively increase pro-collagen I and/or hyaluronic acid production in human dermal fibroblast cells.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

What is claimed is:

1. A method for diminishing the appearance of dermatological signs of aging comprising topically applying to the skin a composition comprising, in a topically acceptable vehicle, a peptide consisting of from 3 to 12 amino acids corresponding to a sequence of GDF11, or a salt, ester, or prodrug thereof, wherein said peptide increases collagen production in skin and/or increases hyaluronic acid production in skin,
wherein said sequence of GDF11 comprises MVV.

2. The method according to claim 1, wherein said dermatological signs of aging include the appearance of fine lines and wrinkles.

3. The method according to claim 1, wherein said peptide increases collagen production in skin.

4. The method according to claim 1, wherein said peptide increases hyaluronic acid production in skin.

5. The method according to claim 1, wherein said composition is applied at least once daily for at least one week.

6. The method according to claim 1, wherein said skin is human skin.

7. The method according to claim 1, wherein said peptide consists of from 3 to 8 amino acids corresponding to a sequence of GDF11.

8. The method according to claim 1, wherein said peptide consists of from 3 to 6 amino acids corresponding to a sequence of GDF11.

9. The method according to claim 1, wherein said peptide consists of MVV.

10. The method according to claim 1, wherein said peptide consists of three or four consecutive amino acids corresponding to a sequence of GDF11.

11. The method according to claim 1, wherein said peptide further comprises a hydrocarbon chain on the amino terminus.

12. The method according to claim 11, wherein said hydrocarbon chain is a $C_{1-24}$ aliphatic hydrocarbon.

13. The method according to claim 12, wherein said composition comprises a prodrug of said peptide, wherein said prodrug includes N-acetyl derivatives of said peptide.

* * * * *